United States Patent
Ono

(10) Patent No.: US 11,184,311 B2
(45) Date of Patent: *Nov. 23, 2021

(54) COMMUNICATION SYSTEM AND COMMUNICATION CONTROL METHOD

(71) Applicant: SONY CORPORATION, Tokyo (JP)

(72) Inventor: Hideyuki Ono, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,351

(22) Filed: Apr. 14, 2020

(65) Prior Publication Data

US 2020/0244613 A1    Jul. 30, 2020

Related U.S. Application Data

(63) Continuation of application No. 15/759,414, filed as application No. PCT/JP2016/073177 on Aug. 5, 2016, now Pat. No. 10,680,990.

(30) Foreign Application Priority Data

Nov. 13, 2015    (JP) .................................. 2015-222865

(51) Int. Cl.
*H04L 12/58*    (2006.01)
*G06F 16/9535*    (2019.01)
(Continued)

(52) U.S. Cl.
CPC .............. *H04L 51/26* (2013.01); *G06F 13/00* (2013.01); *G06F 16/24578* (2019.01);
(Continued)

(58) Field of Classification Search
None
See application file for complete search history.

(56) References Cited

U.S. PATENT DOCUMENTS

2003/0003964 A1* 1/2003 Wroblewski ........ H04M 1/7243
455/567
2004/0066932 A1* 4/2004 Seligmann .............. H04L 51/38
379/373.01
(Continued)

FOREIGN PATENT DOCUMENTS

JP    2002-101211 A    4/2002
JP    2007-26429 A    2/2007
(Continued)

OTHER PUBLICATIONS

International Search Report dated Oct. 18, 2016 in PCT/JP2016/073177 filed Aug. 5, 2016.
(Continued)

*Primary Examiner* — Brian Whipple
(74) *Attorney, Agent, or Firm* — Oblon, McClelland, Maier & Neustadt, L.L.P.

(57) ABSTRACT

Aspects of the present application provide a communication system that includes a communication unit and a control unit. The communication unit is configured to receive, from a communication source, a scheduling request for scheduling transmission of a message to a specific communication destination. The control unit is configured to perform control such that the communication destination is notified of existence of the message at a predetermined timing in accordance with content of the message and a current or past psychological situation of a user corresponding to the specific communication destination received by the communication unit.

20 Claims, 12 Drawing Sheets

(51) Int. Cl.
  *G06F 16/2457* (2019.01)
  *H04M 11/00* (2006.01)
  *G06F 13/00* (2006.01)
  *H04M 11/10* (2006.01)
  *H04M 1/72436* (2021.01)
  *H04M 1/72448* (2021.01)
  *A61B 5/16* (2006.01)

(52) U.S. Cl.
  CPC .......... *G06F 16/9535* (2019.01); *H04L 51/14* (2013.01); *H04L 51/22* (2013.01); *H04L 51/24* (2013.01); *H04M 11/00* (2013.01); *H04M 11/10* (2013.01); *A61B 5/165* (2013.01); *H04M 1/72436* (2021.01); *H04M 1/72448* (2021.01)

(56) References Cited

U.S. PATENT DOCUMENTS

| | | |
|---|---|---|
| 2004/0147814 A1 | 7/2004 | Zancho et al. |
| 2006/0218032 A1* | 9/2006 | Patrick ................ H04M 3/5191 705/1.1 |
| 2006/0230117 A1 | 10/2006 | Gross |
| 2006/0293838 A1 | 12/2006 | Yamamoto et al. |
| 2006/0294225 A1 | 12/2006 | Grecco |
| 2009/0249222 A1* | 10/2009 | Schmidt ................ H04L 51/32 715/751 |
| 2010/0082751 A1* | 4/2010 | Meijer .................... G06F 15/16 709/206 |
| 2010/0223341 A1* | 9/2010 | Manolescu ........... H04L 51/063 709/206 |
| 2012/0052905 A1* | 3/2012 | Lim ........................ G06F 3/015 455/550.1 |
| 2012/0059787 A1 | 3/2012 | Brown |
| 2012/0123854 A1 | 5/2012 | Anderson et al. |
| 2013/0339453 A1* | 12/2013 | Aggarwal ............. H04W 4/021 709/206 |
| 2014/0136989 A1 | 5/2014 | Choi |
| 2014/0288401 A1 | 9/2014 | Ouwerkerk et al. |
| 2015/0051501 A1 | 2/2015 | Dugan |
| 2015/0195378 A1 | 7/2015 | Kano et al. |
| 2015/0264145 A1 | 9/2015 | Cudak et al. |
| 2015/0264146 A1 | 9/2015 | Cudak et al. |
| 2016/0019402 A1* | 1/2016 | Khandelwal ........ G06F 21/6254 726/26 |
| 2018/0109482 A1 | 1/2018 | DeLuca |

FOREIGN PATENT DOCUMENTS

| | | |
|---|---|---|
| JP | 2007-207153 A | 8/2007 |
| JP | 2010-176615 A | 8/2010 |
| JP | 2012-108916 A | 6/2012 |
| JP | 2015-5207 A | 1/2015 |
| JP | 2015-503937 A | 2/2015 |
| JP | 2015-149536 A | 8/2015 |
| WO | 2014/013886 A1 | 1/2014 |

OTHER PUBLICATIONS

Extended European Search Report dated Sep. 10, 2018 in corresponding European Patent Application No. 16863858.3, 8 pages.

* cited by examiner

FIG. 5

| DATE AND TIME | TRANSMISSION SOURCE ID | TRANSMISSION DESTINATION ID | CONTENT | TYPE | WEATHER | SCHEDULE | HEARTBEATS BEFORE RECEPTION | HEARTBEATS AFTER RECEPTION | QUESTIONNAIRE RESULT | | |
|---|---|---|---|---|---|---|---|---|---|---|---|
| | | | | | | | | | SENSE OF SECURITY | HONESTY | SENSE OF AFFINITY |
| 2014/02/20 10:00 | aaa | bbb | Your recital will be on tomorrow! I believe in you! | ENCOURAGEMENT | CLOUDY | NONE | 150 | 140 | 4 | 3 | 4 |
| 2014/08/20 12:00 | aaa | bbb | Your recital will be on tomorrow! You can do it! | ENCOURAGEMENT | RAINY | SCHOOL | 140 | 180 | 3 | 2 | 3 |
| 2015/08/17 14:00 | aaa | ccc | We got lucky with great weather! By, the way, I ate your ice cream in the fridge. Sorry! | APOLOGY | SUNNY | NONE | 140 | 120 | 3 | 4 | 5 |
| 2015/08/22 16:00 | aaa | bbb | Your recital will be on the day after tomorrow! I believe in you! | ENCOURAGEMENT | SUNNY | NONE | 200 | 160 | 5 | 3 | 4 |
| ... | ... | ... | ... | ... | ... | ... | ... | ... | ... | ... | ... |

FIG. 10

| TIME | SCHEDULE | WEATHER FORECAST | BEHAVIOR PREDICTION | ESTIMATED HEARTBEATS |
|---|---|---|---|---|
| 14:00 — 18:00 | SCHOOL | CLOUDY HUMIDITY 0% | | 80 |
| | | | | 70 |
| | EXTRACURRICULAR ACTIVITY | | | 120 |
| 18:00 — 22:00 | | | | |
| 22:00 — 02:00 | | SUNNY HUMIDITY 0% | SLEEPING | |
| 02:00 — 06:00 | | | | |
| 06:00 — 10:00 | | CLOUDY HUMIDITY 0% | | |
| 10:00 — 14:00 | SCHOOL | | | 80 |

What did you feel about the message transmitted
from your younger sister yesterday?

Did you feel a sense of security?

NO [====] YES

Did you feel honesty?

NO [====] YES

Did you feel a sense of affinity?

NO [====] YES

ANSWER — 421

FIG. 12

| DATE | SCHEDULE | WEATHER FORECAST | BEHAVIOR PREDICTION | ESTIMATED HEARTBEATS |
|---|---|---|---|---|
| 18 | SCHOOL | | SLEEPING | 110 |
| 19 | SCHOOL | CLOUDY HUMIDITY O% | SLEEPING | 110 |
| 20 | SCHOOL | | SLEEPING | 110 |
| 21 | SCHOOL | | SLEEPING | 110 |
| 22 | LESSON | RAINY HUMIDITY O% | SLEEPING | 120 |
| 23 | PRACTICE | CLOUDY HUMIDITY O% | | 100 |

COMMUNICATION SYSTEM AND COMMUNICATION CONTROL METHOD

CROSS REFERENCE

This present application is a continuation application of U.S. patent application Ser. No. 15/759,414 filed on Mar. 12, 2018, which is a National Stage application of PCT/JP2016/073177 filed on Aug. 5, 2016, which claims the benefit of priority to Japan Patent Application No. 2015-222865 filed on Nov. 13, 2015. The entire disclosures of the prior applications are hereby incorporated by reference in their entirety.

TECHNICAL FIELD

The present disclosure relates to communication systems and communication control methods.

BACKGROUND ART

In recent years, communication technologies have been developed, and messages have been frequently exchanged via networks. It is possible for users to check messages transmitted from other terminals or to transmit messages by using information processing terminals such as smartphones, mobile phone terminals, and tablet terminals.

With regard to such a message transmission and reception system, for example, Patent Literature 1 listed below describes a device configured to variably control content of a message to a user and its transmission timing in accordance with context (internal and external states) of the user. In addition, Patent Literature 2 listed below describes a system in which devices transmit and receive appropriate information to and from each other in accordance with feelings and/or behavior of users. In addition, Patent Literature 3 listed below describes a delivery service system configured to transmit voice information on a date designated through delivery scheduling.

CITATION LIST

Patent Literature

Patent Literature 1: JP 2015-5207A
Patent Literature 2: JP 2007-207153A
Patent Literature 3: JP 2002-101211A

DISCLOSURE OF INVENTION

Technical Problem

Here, sometimes a receiver of a transmitted message has different feelings depending on timings of reading the received message. In general, in the case where a message is transmitted via e-mail, online chat, or the like, the message is delivered to a receiver in almost real time. Therefore, for example, the user wants to guess a current feeling of the receiver and transmit an apology or invitation message at an optimal timing. However, there is no way to know the current feeling of the receiver, and it is difficult to transmit such a message at the optimal timing. In addition, the optimal timing differs depending on content of the message.

Note that, Patent Literature 1 described above is a technology of transmitting a message to himself/herself to control his/her motivation to achieve his/her goal. Therefore, it is difficult to solve the above described problem by using Patent Literature 1. In addition, Patent Literature 2 described above is a technology of recommending contents such as music in accordance with a feeling and/or behavior at that time, to meet his/her preference that changes in real time. Therefore, it is difficult to solve the above described problem by using Patent Literature 2. In addition, Patent Literature 3 described above is a technology for a user to designate a date and time to transmit voice information to another user. Therefore, it is difficult to solve the above described problem by using Patent Literature 3.

Accordingly, the present disclosure proposes a communication system and a communication control method that are capable of receiving a transmission schedule and performing control such that a receiver is notified of a message at an optimal timing in view of content of the message and a psychological situation of the receiver.

Solution to Problem

According to the present disclosure, there is provided a communication system including: a communication unit configured to receive, from a communication source, a scheduling request for scheduling transmission of a message to a specific communication destination; and a control unit configured to perform control such that the communication destination is notified of existence of the message at a predetermined timing in accordance with content of the message and a current or past psychological situation of a user corresponding to the specific communication destination received by the communication unit.

According to the present disclosure, there is provided a communication control method including, by a processor: receiving, from a communication source, a scheduling request for scheduling transmission of a message to a specific communication destination; and performing control such that the communication destination is notified of existence of the message at a predetermined timing in accordance with content of the message and a current or past psychological situation of a user corresponding to the received specific communication destination.

Advantageous Effects of Invention

As described above, according to the present disclosure, it is possible to receive a transmission schedule and perform control such that a receiver is notified of a message at an optimal timing in view of content of the message and a psychological situation of the receiver.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 5 is a diagram illustrating an example of various kinds of data stored in storage units according to the embodiment.

FIG. 10 is a diagram illustrating an example of a heartbeat estimation result of a user B according to a first example.

FIG. 11 is a diagram illustrating an example of a questionnaire input screen according to the embodiment.

FIG. 12 is a diagram illustrating an example of a heartbeat estimation result of a user C according to a second example.

MODE(S) FOR CARRYING OUT THE INVENTION

Figure 1:
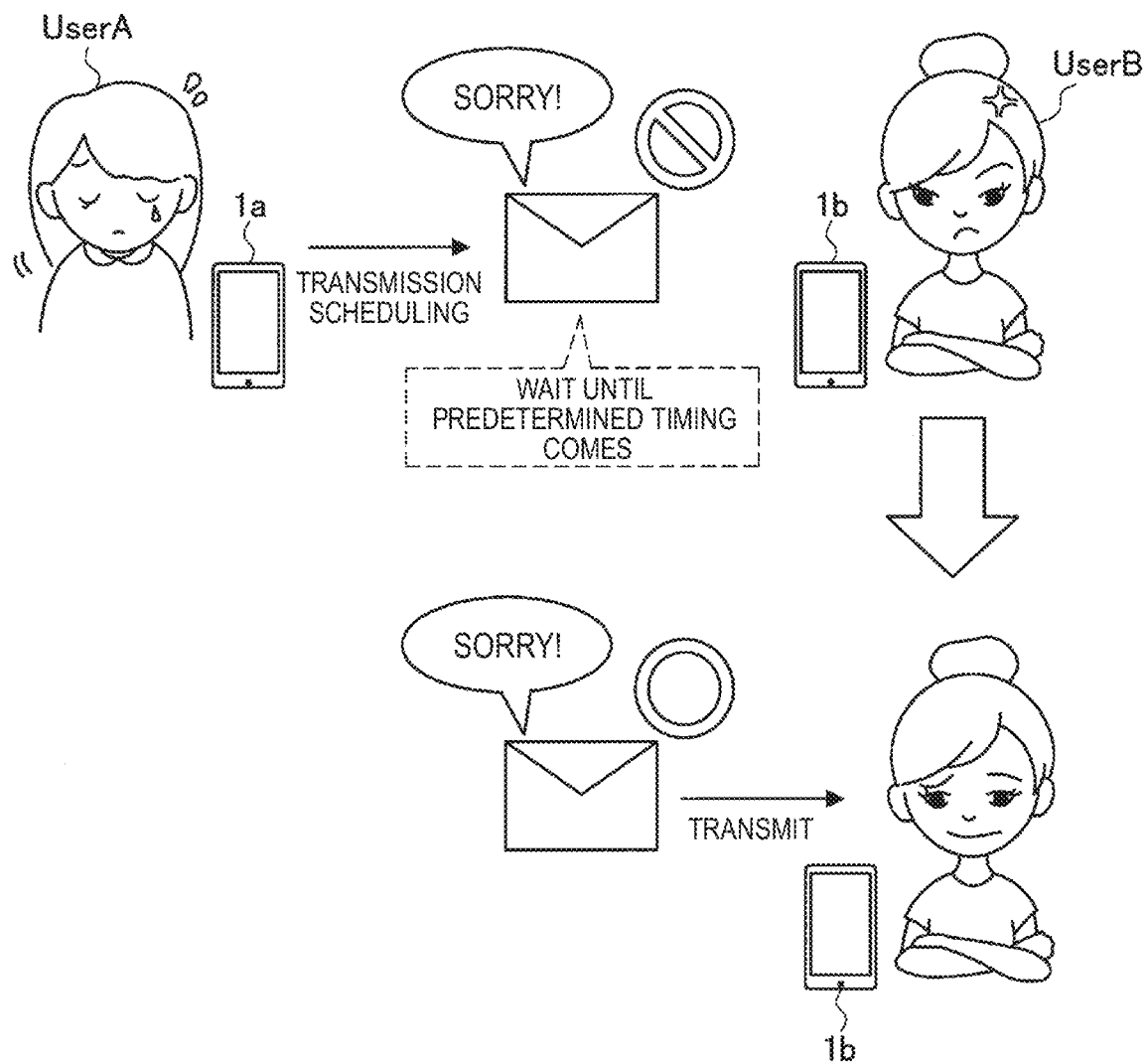
FIG. 1 is a diagram illustrating an application example of an information processing system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description is given in the following order.
1. Overview of information processing system according to embodiment of present disclosure
2. Configuration
2-1. Configuration of user terminal
2-2. Configuration of server
3. Operation process
3-1 Message communication control process
3-2. Appropriate time slot determination process of apology or encouragement message
3-3. Appropriate time slot determination process of invitation message
4. Examples
4-1. Example of apology message
4-2. Example of encouragement message
5. Conclusion

1. Overview of Information Processing System According to Embodiment of Present Disclosure By using an information processing system according to an embodiment of the present disclosure, it is possible to receive a transmission schedule and perform control such that a receiver is notified of a message at an optimal timing in view of content of the message and a psychological situation of the receiver. Next, with reference to FIG. 1, an application example of the information processing system according to the embodiment will be described.

FIG. 1 is a diagram illustrating the application example of the information processing system according to the embodiment of the present disclosure. For example, when a user A (communication source) transmits an apology message to a user B (communication destination), the user A wants to transmit the message at a timing at which the user B is in a good mood, or at least a timing other than a timing at which the user B is in a bad mood. However, it is difficult to know feelings of the user B. Therefore, the information processing system according to the embodiment receives a transmission scheduling request of a message to the user B from the user A, and controls a transmission timing of the message in accordance with psychological situations of the user B.

For example, as illustrated in FIG. 1, control is performed such that an apology e-mail whose transmission scheduling request has been issued by the user A is not transmitted and enters a standby state while the user B is in a bad mood, and the apology e-mail is transmitted when the user B gets in a good mood. This can establish better communication. In addition, it is also possible to improve impression that the user B has by automatically editing the message to include content regarding a recent fact.

Note that, the message is transmitted and received via user terminals 1 such as smartphones, mobile phone terminals, tablet terminals, wearable terminals (such as smart bands, smartglasses, or smartwatches), or personal computers (PCs).

In addition, for example, a real-time psychological situation of the user B is estimated on the basis of sensor data (such as acceleration data, positional data, cardinal direction data, vibration data, sound data, captured image data, pulse data, heartbeat data, body temperature data, sweat amount data, brain wave data, or the like) detected by various kinds of sensors installed in a wearable terminal 10 worn by the user B or various kinds of sensors installed in a user terminal 1b. The sensor data detected by the wearable terminal 10 is transmitted to the user terminal 1b via Wi-Fi (registered trademark) or near-field communication such as Bluetooth (registered trademark).

In addition, in this embodiment, a heartbeat log or behavior recognition results (heartbeat history and behavior recognition history) are continuously acquired on the basis of the sensor data, and are used for determining an appropriate time slot of a notification timing at which a server 2 notifies of a message. Note that, it is also possible to configure the setting such that the heartbeat log and the behavior recognition results are not always acquired. In other words, when determining a message notification timing, the various kinds of sensors installed in the wearable terminal 10 or the user terminal 1b are intermittently activated. This achieves electric power saving. In addition, it is also possible for another system to acquire the heartbeat log and the behavior recognition results of the user B, and refer to them as necessary in conjunction with the information processing system according to the embodiment.

In addition, a schedule of a transmission destination user or weather information may also be used when the server 2 determines an appropriate time slot of the message notification timing. The server 2 appropriately acquires data from an external schedule server 4a or an external weather information server 4b via a network 3.

Figure 2:
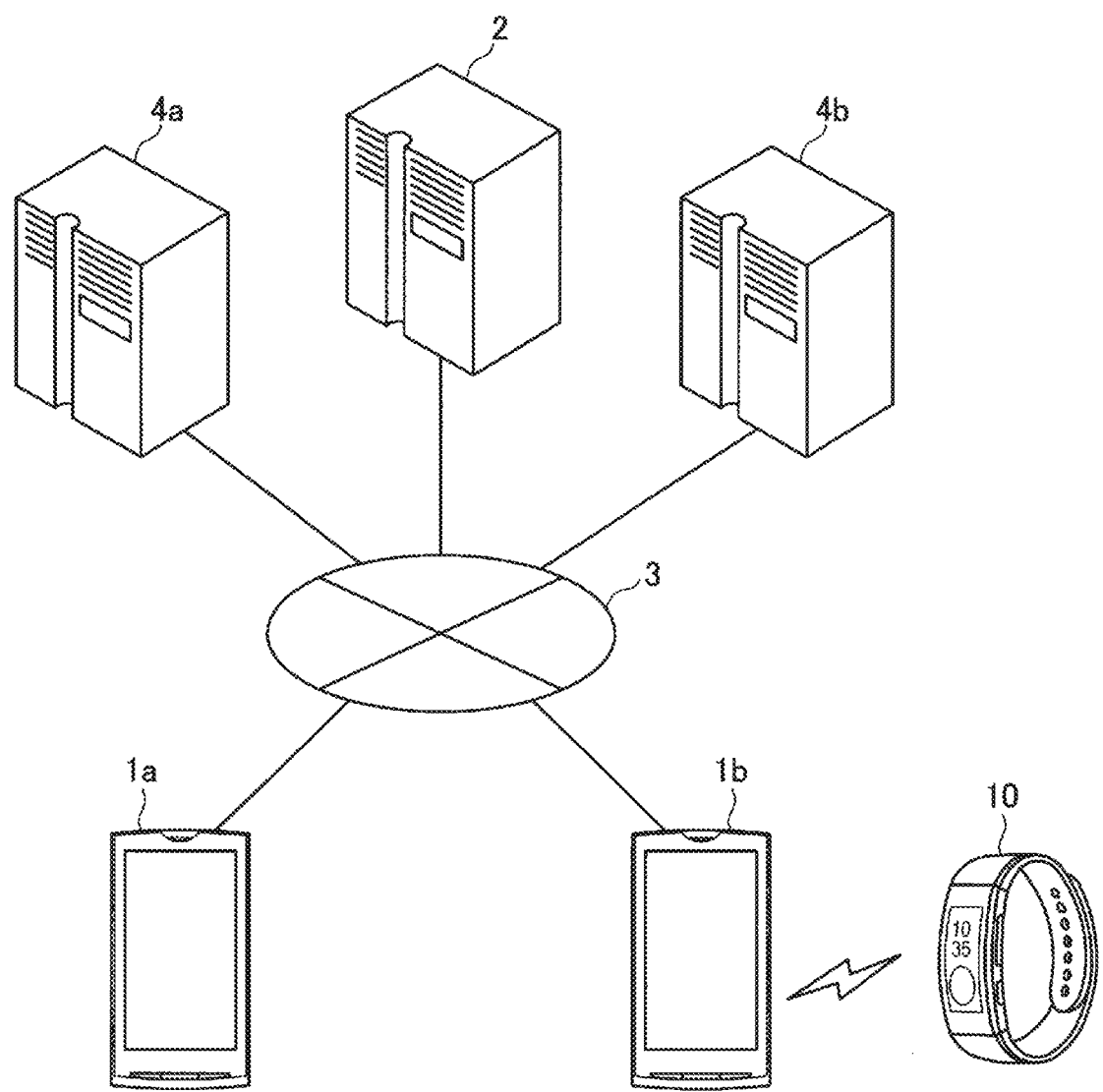
FIG. 2 is a diagram illustrating an overall configuration of the information processing system according to the embodiment.

Next, with reference to FIG. 2, an overall configuration of the information processing system according to the embodiment will be described. FIG. 2 is a diagram illustrating the overall configuration of the information processing system according to the embodiment.

As illustrated in FIG. 2, the information processing system according to the embodiment includes a user terminal 1a serving as the communication source, a user terminal 1b serving as the communication destination, the wearable terminal 10, and the server 2. The wearable terminal 10 is configured to acquire sensor data to be used for estimating psychological situations of a communication destination user. Note that, here, for example, the user terminals 1a and 1b are distinguished from each other as a communication source terminal and a communication destination terminal. However, the embodiment is not limited thereto. The user terminals 1a and 1b are implemented as user terminals 1 having the same configuration, and it is possible to use the user terminals 1a and 1b as any of the communication source and the communication destination.

The server 2 connects with the user terminals 1a and 1b via the network 3 and transmits/receives data. Specifically, the server 2 receives a scheduling request from the user terminal 1a, the scheduling request scheduling transmission of a message to a specific communication destination (here, the user terminal 1b). Subsequently, the server 2 performs control such that the user terminal 1b is notified of existence of the message at a predetermined timing in accordance with content of the message and psychological situations of the user corresponding to the specific communication destination. For example, the psychological situations of the user are acquired by the wearable terminals 10 worn by the user of the communication destination, and estimated by the server 2 on the basis of sensor data transmitted from the user terminal 1b to the server 2 via the network 3.

The overview of the information processing system according to the embodiment has been described above. Next, with reference to FIG. 3 to FIG. 4, detailed configurations of the user terminals 1 and the server 2 included in the information processing system according to the embodiment will be described.

2. Configuration

<2-1. Configuration of User Terminal>

Figure 3:
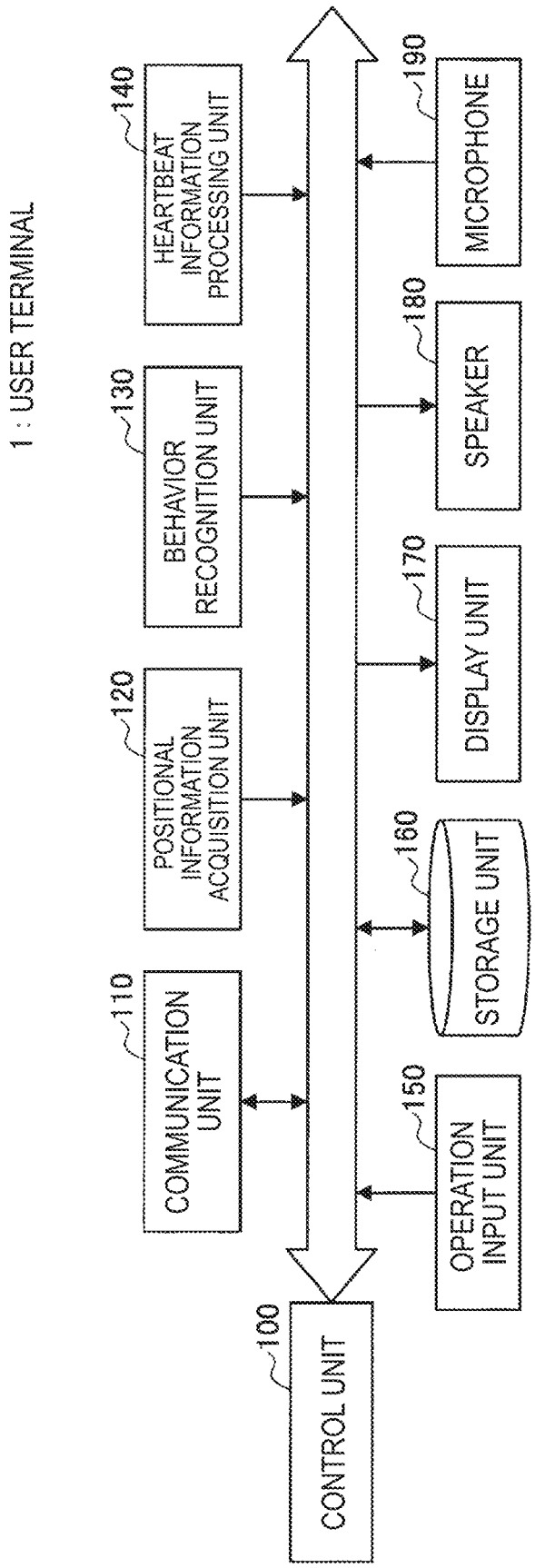
FIG. 3 is a block diagram illustrating an example of a configuration of a user terminal according to the embodiment.

FIG. 3 is a block diagram illustrating a configuration example of the user terminal 1 according to the embodiment. As illustrated in FIG. 3, the user terminal 1 includes a control unit 100, a communication unit 110, a positional information acquisition unit 120, a behavior recognition unit 130, a heartbeat information processing unit 140, an operation input unit 150, a storage unit 160, a display unit 170, a speaker 180, and a microphone 190.

The control unit 100 functions as an arithmetic processing device and a control device, and controls the overall operation in the user terminal 1 in accordance with various programs. For example, the control unit 100 is implemented as a central processing unit (CPU), or an electronic circuit such as a microprocessor or the like.

The communication unit 110 exchanges data with an external device in a wired/wireless manner. For example, the communication unit 110 connects with the server 2 via the network 3, and transmits a text message input via the operation input unit 150. In addition, the communication unit 110 further includes a function of exchanging data with the wearable terminal 10 via Wi-Fi or near-field communication such as Bluetooth.

The positional information acquisition unit 120 has a function of acquiring positional information of the user terminal 1. For example, the positional information acquisition unit 120 may be a Global Positioning System (GPS) antenna and a GPS process unit configured to process GPS signals received via the GPS antenna. Alternatively, the positional information acquisition unit 120 may be a Wi-Fi antenna configured to receive Wi-Fi (registered trademark) radio waves from a plurality of base stations, and a position calculation unit configured to estimate distances from the respective base stations from reception intensities of received Wi-Fi radio waves, and calculate a current position on the basis of a principle of triangulation using the distances from the respective base stations and positions of the respective base stations.

The behavior recognition unit 130 recognizes user behavior on the basis of sensor data detected by various kinds of sensor installed in the user terminal 1 or the wearable terminal 10. For example, the behavior recognition unit 130 recognizes behavior of the user on the basis of the positional information acquired by the positional information acquisition unit 120, acceleration data detected by the acceleration sensor (not illustrated), heartbeat information acquired by the heartbeat information processing unit 140, and the like. Examples of the behavior of the user include attitudes such as sitting/standing, movement such as walking/running, and contexts (states of the user) such as awakening/sleeping/working in office/studying in school/traveling by train.

The heartbeat information processing unit 140 acquires heartbeat information of the user, trims data through a noise processing as necessary, and outputs heartbeat information to the control unit 100. For example, the heartbeat information processing unit 140 acquires heartbeat information on the basis of sensor data detected by the heartbeat sensor installed in the wearable terminal 10.

The operation input unit 150 is implemented as a touchscreen, a switch, a button, or the like. The operation input unit 150 detects operation input by the user, and outputs the detected input signal to the control unit 100. For example, the operation input unit 150 outputs a text message input by the user to the control unit 100.

The storage unit 160 is implemented as read only memory (ROM) or random access memory (RAM). The ROM stores programs, operation parameters, and the like that are used in processes performed by the control unit 100, and the RAM temporarily stores a parameters and the like that arbitrarily change.

The display unit 170 is an example of the output unit. The display unit 170 is implemented as a display device such as a liquid crystal display (LCD) device, or an organic light emitting diode (OLED) display device.

The speaker 180 is an example of the output unit. The speaker 180 has a function of reproducing sound signals.

The microphone 190 collects surrounding sound and outputs the collected sound data to the control unit 100. For example, the microphone 190 collects speech voice of the user and output it to the control unit 100 as a voice message. The control unit 100 may transmit the collected sound data to the server 2 as the voice message, or may generate a text message through a speech recognition process and transmit it to the server 2.

The detailed configuration of the user terminal 1 according to the embodiment has been described above. Note that, the configuration of the user terminal 1 according to the embodiment is not limited to the example illustrated in FIG. 3. For example, the user terminal 1 may further include a camera, a distance sensor, an environment sensor, or the like.

<2-2. Configuration of Server>

Figure 4:
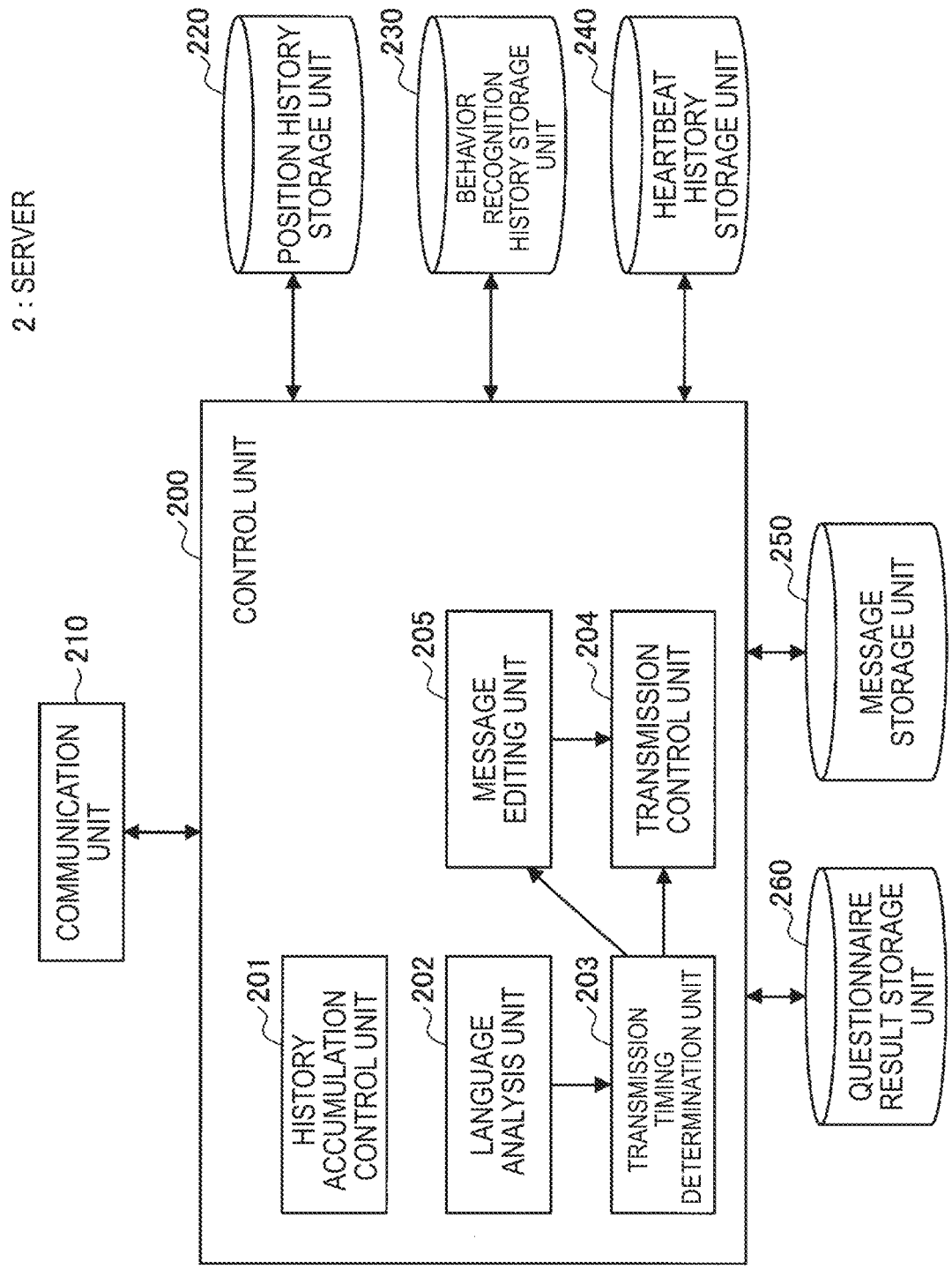
FIG. 4 is a block diagram illustrating an example of a configuration of a server according to the embodiment.

FIG. 4 is a block diagram illustrating an example of the configuration of the server 2 according to the embodiment. As illustrated in FIG. 3, the server 2 includes a control unit 200, a communication unit 210, a position history storage unit 220, a behavior recognition history storage unit 230, a heartbeat history storage unit 240, a message storage unit 250, and a questionnaire result storage unit 260.

The communication unit 210 exchanges data with an external device in a wired/wireless manner. For example, the communication unit 210 receives a message transmission scheduling request from the user terminal 1 serving as the communication source. In addition, the communication unit 210 transmits a message to the user terminal 1 serving as the communication destination under the control of a transmission control unit 204 (to be described later).

The control unit 200 functions as an arithmetic processing device and a control device, and controls the overall operation in the server 2 in accordance with various programs. For example, the control unit 200 is implemented as an electronic circuit such as a CPU or a microprocessor. In addition, the control unit 200 according to the embodiment also functions as a history accumulation control unit 201, a language analysis unit 202, a transmission timing determination unit 203, a transmission control unit 204, and a message editing unit 205.

The history accumulation control unit 301 controls the position history storage unit 220, the behavior recognition history storage unit 230, and the heartbeat history storage unit 240 to respectively accumulate positional information, behavior recognition results, and heartbeat data of users received from the respective user terminals 1, as a position history, a behavior recognition history, and a heartbeat history of the respective user in addition to its date and time.

The language analysis unit 202 analyzes content (meaning and overview) of a message in the message transmission scheduling request transmitted from the user terminal 1.

The transmission timing determination unit 203 determines a predetermined timing at which the user terminal 1 serving as the transmission destination is notified of existence of the scheduled message, in accordance with a result of message analysis performed by the language analysis unit 202 and current and past psychological situations of the user corresponding to the transmission destination of the message whose transmission scheduling request has been issued.

Specifically, for example, the transmission timing determination unit 203 determines an appropriate time slot for a psychological situation in accordance with a type of the message (such as "apology", "encouragement", or "invitation") based on the message analysis result. It is determined when the user enters various psychological situations, on the basis of a past heartbeat history corresponding to the behavior recognition history and the position history of the transmission destination user, the schedule information of the transmission destination user, and weather forecast information. In this embodiment, for example, the heartbeat history is used for estimating psychological situations of the user.

In other words, the transmission timing determination unit 203 recognizes types of heartbeats (in other words, psychological situations) depending on types of behaviors of the transmission destination user, on the basis of a past heartbeat history corresponding to the behavior recognition history, and predicts change in the psychological situations of the user in accordance with schedule information of the transmission destination user. Subsequently, the transmission timing determination unit 203 determines a time slot in which the user enters a psychological situation appropriate to the message.

In addition, the transmission timing determination unit 203 is capable of acquiring weather information (weather, humidity, temperature, a discomfort index, or the like) in a place where the transmission destination user is present on the basis of weather information corresponding to positional information, and recognizing types of heartbeats (in other words, psychological situations) depending on various weather situation in view of a heartbeat history at that time. Next, the transmission timing determination unit 203 predicts change in the psychological situation of the user by using schedule information (used for estimating places the user will visit) of the transmission destination user and weather forecast information (weather forecast information of the places the user will visit). Subsequently, the transmission timing determination unit 203 determines a time slot in which the user enters a psychological situation appropriate to the message.

Alternatively, it is also possible for the transmission timing determination unit 203 to recognize tendencies indicating when and how the heartbeats (in other words, psychological situation) change by using the heartbeat history, and determine a time slot of a psychological situation appropriate to the message on the basis of the state of the heartbeats.

In the above described example, the time slot of the psychological situation appropriate to the type of the message has been mainly described. However, the embodiment is not limited thereto. It is also possible to determine a time slot of a psychological situation appropriate to expression (wording) used in the message. Specifically, the transmission timing determination unit 203 acquires a date and time at which a message in which the same expression is used as the message whose scheduling request has been issued by the transmission destination user from the message storage unit 250, and acquires a heartbeat history of the transmission destination user at the date and time from the heartbeat history storage unit 240. Next, the transmission timing determination unit 203 recognizes what kind of heartbeats (in other words, psychological situations) means that the user of the transmission destination is in a better psychological situation when receiving the message with such an expression. Next, on the basis of the heartbeat history, the transmission timing determination unit 203 determines a time slot of a psychological situation appropriate for transmitting the message whose scheduling request has been issued this time.

In addition, when determining the time slot of the psychological situation appropriate to the expression (wording) used in the message, it is also possible for the transmission timing determination unit 203 to use the heartbeat history and a result of a questionnaire related to a psychological situation of the transmission destination user at a time of receiving a message with the same expression. The result of the questionnaire is acquired from the questionnaire result storage unit 260.

The transmission control unit 204 performs control such that the message is transmitted in the appropriate time slot determined by the transmission timing determination unit 203. At this time, the transmission control unit 204 may acquire a real-time psychological situation or a real-time behavior recognition result of the transmission destination user in the appropriate time slot, and may perform control such that the message is transmitted at a timing at which the user enters an optimal psychological situation or the user exhibits optimal behavior (also referred to as an "appropriate timing"). In this embodiment, the transmission of a message means transmission of a body of the message, transmission of only a title or a sender of the message, or transmission of a notification indicating existence of the message (such as a message "new e-mail is arrived in the server").

In addition, in the embodiment, the "predetermined timing" includes the "appropriate time slot" and the "appropriate timing" described above.

The message editing unit 205 has a function of automatically editing a message to be transmitted from the transmission control unit 204 to the transmission destination user. Specifically, the message editing unit 205 inserts a text into the message, the text describing an event occurred after receiving the scheduling request. Accordingly, it is possible to prevent the transmission destination user from knowing that the message is accumulated in the server 2 in a certain period of time, and this achieves more natural communication. In addition, when editing the message to include words of season's greetings at the top of the message as the text describing the event, such season's greeting words can lead a main topic of the message.

In addition, it is also possible for the message editing unit 205 to change content of a message whose scheduling request has been issued, on the basis of content of a past received message to the transmission destination user and a psychological situation of the transmission destination user at the time of receiving the received message. In this way, for example, it is possible to change or add the expression that makes the psychological situation of the transmission destination user better.

In addition, it is also possible for the message editing unit 205 to reproduce the message whose scheduling request has been issued, by voice of a predetermined pop star such as a pop star the transmission destination user likes. In this way, for example, it is possible to make the psychological situation of the transmission destination user who has received the message better.

The position history storage unit 220 stores positional information of the respective user terminals 1 as position histories of the respective users in association with date and time, under the control of the history accumulation control unit 201. In this embodiment, the respective users may be identified by using user IDs, for example.

The behavior recognition history storage unit 230 stores behavior recognition results of the respective user terminals 1 as behavior recognition histories of the respective users in association with date and time, under the control of the history accumulation control unit 201.

The heartbeat history storage unit 240 stores heartbeat information of the respective user terminals 1 as heartbeat histories of the respective users in association with date and time, under the control of the history accumulation control unit 201.

The message storage unit 250 stores messages transmitted and received to and from the respective user terminals 1 as transmission/reception histories of the respective users in association with date and time. In addition, the message storage unit 250 also stores transmission scheduling request messages received from the user terminals 1.

The questionnaire result storage unit 260 stores questionnaire results transmitted from the respective user terminals 1 in association with date and time.

The above-described data pieces stored in the respective storage units are association with each other by using date, time, and user IDs as a key. Here, FIG. 5 illustrates an example of various kinds of data stored in the storage units according to the embodiment. The illustrated data is various kinds of data associated with histories of past messages transmitted by a user (user ID: aaa) of a transmission source who has issued the message transmission scheduling request. Specifically, message transmission date and time, transmission source IDs, transmission destination IDs, content of messages (automatically-editing parts may be displayed in an identifiable manner), types of messages, weather at a time of reception, a schedule of the transmission destination user at the time of reception (or behavior recognition results), heartbeats of the transmission destination user before and after the reception, questionnaire results of the transmission destination users. In the questionnaire result, the transmission destination user inputs evaluation of the message in view of a sense of security, honesty, and a sense of affinity on a five-point scale.

The detailed configuration of the server 2 according to the embodiment has been described above. Note that, the configuration of the server 2 according to the embodiment is not limited to the example illustrated in FIG. 4. For example, another server on the network may include the respective storage units. In addition, the heartbeat history is used for estimating psychological situations of the user. However, the embodiment is not limited thereto. It is also possible to use other biological information (such as sweat amount history, pulse history, or brain wave history). Next, details of operation processes according to the embodiment will be described.

3. Operation Process

<3-1 Message Communication Control Process>

Figure 6:
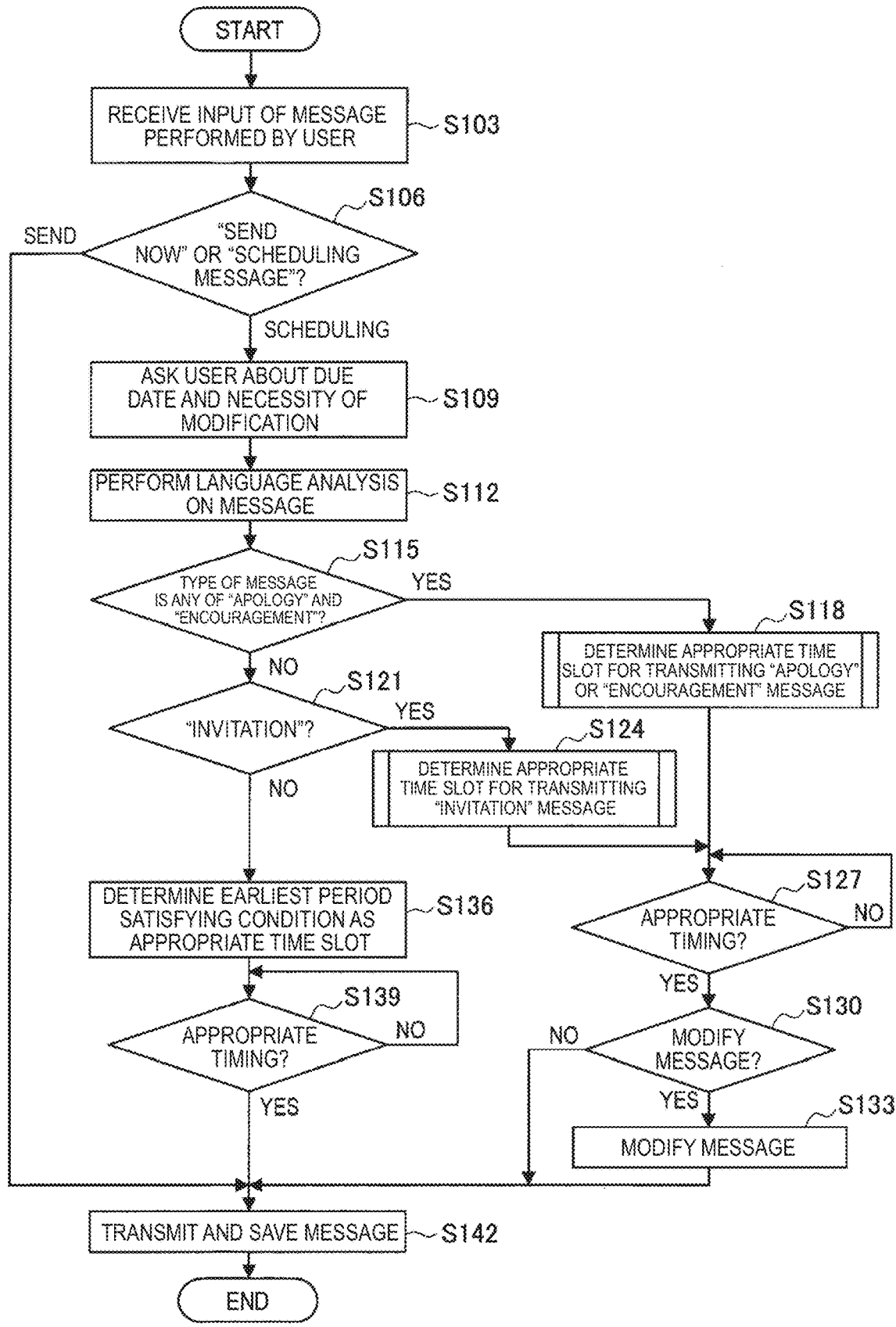
FIG. 6 is a flowchart illustrating a message communication control process according to the embodiment.
Figure 7:
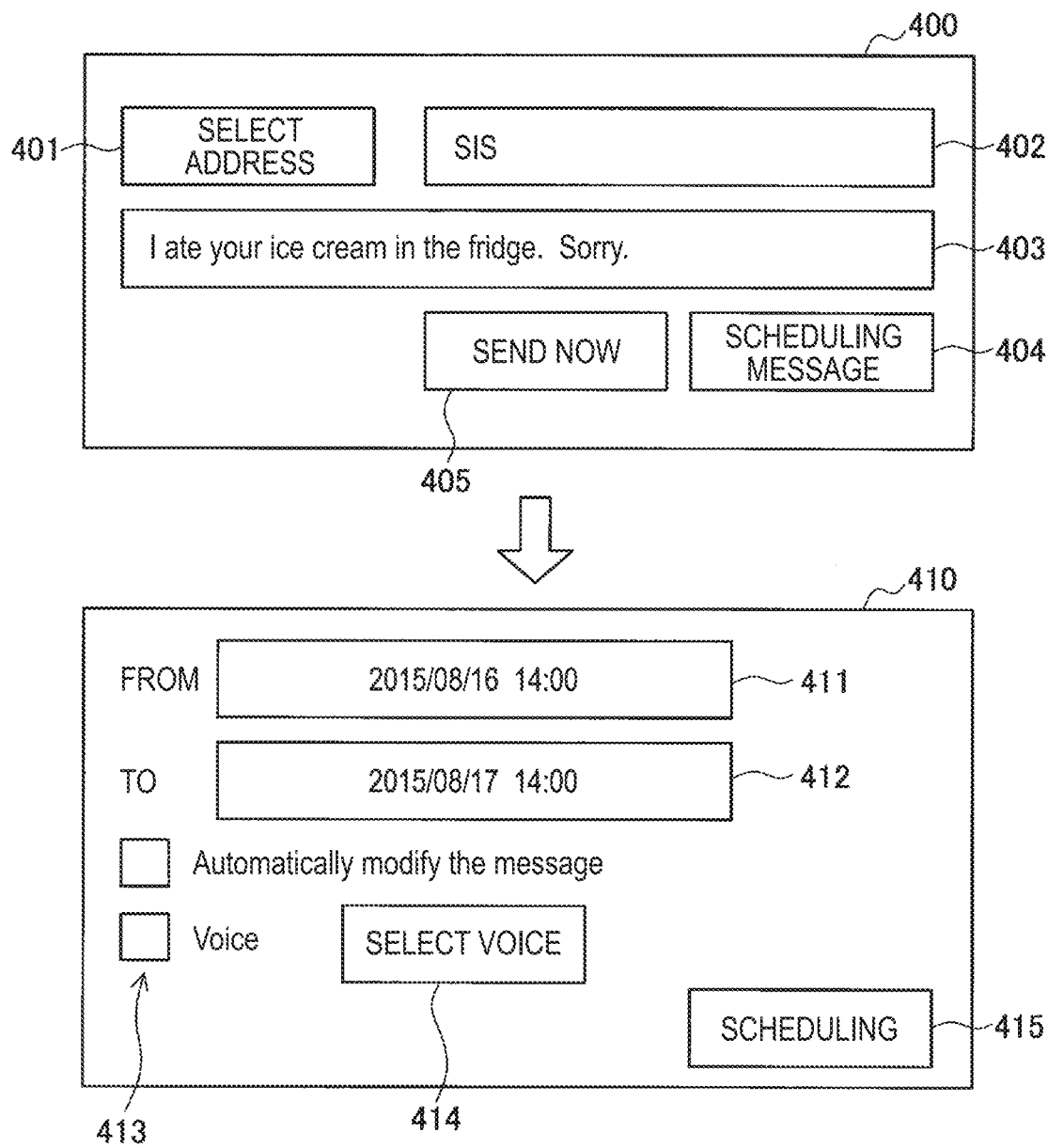
FIG. 7 is a diagram illustrating an example of a message input screen according to the embodiment.

FIG. 6 is a flowchart illustrating a message communication control process according to the embodiment. As illustrated in FIG. 6, the server 2 first receives input of a message performed by a user (Step S103). Specifically, the server 2 acquires the message input by the user via the user terminal 1*a* serving as the transmission source. Here, FIG. 7 illustrates an example of a message input screen displayed on the user terminal 1*a*. A screen 400 illustrated on the upper side of FIG. 7 includes an address selection button 401, an address list 402, a message input field 403, a send button 405, and a scheduling button 404. The user taps the address selection button 401 to select one or more addresses from a plurality of addresses. The one or more selected addresses are displayed in the address list 402. In addition, the user inputs a message into the message input field 403 by using a virtual keyboard (not illustrated) displayed on the screen. Subsequently, in the case of transmitting the message immediately as usual, the user taps a send button 405 "SEND NOW". Alternatively, in the case of issuing a scheduling request according to the embodiment, the user taps the scheduling button 404. In the case where the send button 405 "SEND NOW", the transmission control unit 204 immediately transmits the message to the transmission destination (Step S142).

On the other hand, when the scheduling button 404 is tapped ("SCHEDULING" in Step S106), the server 2 asks the user about a due date for transmitting the message (transmission period) and necessity of modification (automatic editing) (Step S109). Specifically, when the scheduling button 404 is tapped, the display screen of the user terminal 1*a* transitions to a screen 410 illustrated in the bottom side of the FIG. 7. The screen 410 includes a transmission period start date and time designation field 411, a transmission period expiration date and time designation field 412, modification selection boxes 413, and a scheduling button 415. The "transmission period" means a period from an earliest message transmission start date and time input into the start date and time designation field 411 to the expiration date and time input into the expiration date and time designation field 412. By using the modification selection boxes, it is possible to select automatic modification of the message and/or voice modification. In the case where the voice modification is selected, it is possible to transmit the input message as a voice message. In addition, it is possible to select voice of the voice message from a voice list (characters, pop stars, and voice actors/actresses) via a voice selection button 414.

Next, the language analysis unit 202 of the server 2 performs language analysis on the message whose scheduling request has been issued by the user (Step S112). Specifically, the language analysis unit 202 recognizes an overview of the message, that is, the type of the message on the basis of semantic analysis, keywords, and the like in addition to semantic analysis of the message and keyword extraction.

Next, in the case where the type of the message is the "apology" or the "encouragement" (YES in Step S115), the transmission timing determination unit 203 determines an appropriate time slot for transmitting the apology or encouragement message (Step S118). For example, the time slot is determined within the transmission period designated by the transmission source user in Step S109. Details of the determination process will be described later with reference to FIG. 8.

On the other hand, in the case where the type of the message is the "invitation" (YES in Step S121), the transmission timing determination unit 203 determines an appropriate time slot for transmitting the invitation message (Step S124). For example, the time slot is determined within the transmission period designated by the transmission source user in Step S109. Details of the determination process will be described later with reference to FIG. 11. Note that, in this embodiment, the predetermined determination processes performed in the case where the type of the message is the "apology", the "encouragement", or the "invitation" has been described as an example. However, the types of the messages are not limited thereto. For example, it is also possible to determine an appropriate time slot for a psychological situation depending on the respective message types in the case where the message type is a "request", a "demand", a "reminder", a "sales", or the like.

Next, when the determined time slot comes, the transmission control unit 204 determines an appropriate timing for transmitting the message to the transmission destination, as a final determination (Step S127). Specifically, the transmission control unit 204 recognizes a current psychological situation on the basis of real-time heartbeat information of the transmission destination user, and determines the best transmission timing.

Next, when the appropriate timing comes (YES in Step S127), the control unit 200 of the server 2 checks whether to modify the scheduled message (Step S130). The modification of the message means automatic modification of the message designated by the transmission source user in Step S109.

Next, in the case where the modification is set (YES in Step S130), the message editing unit 205 modifies the message (Step S133).

Next, at the appropriate timing, the transmission control unit 204 transmits the message whose scheduling request has been issued, to the user terminal 1b serving as the designated transmission destination (Step S142). In addition, the transmitted message is stored in the message storage unit 250 as a transmission/reception history.

Note that, in the case where the type of the message is not the "invitation" (NO in Step S121), the transmission timing determination unit 203 determines an earliest period satisfying a condition as the appropriate time slot, on the basis of the transmission period input by the transmission source user (Step S136). For example, in the case where the "from 14:00 on Xth to 14:00 on the next day" is set as the transmission period, the transmission timing determination unit 203 determines the earliest time slot "from 14:00 to 15:00 on Xth" in that period as the appropriate time slot.

Next, in the case where the appropriate timing comes (YES in Step S139), the transmission control unit 204 transmits the message whose scheduling request has been issued, to the user terminal 1b serving as the designated transmission destination (Step S142). In a way similar to Step S127, the appropriate timing may be determined depending on a psychological situation estimated from real-time heartbeat information of the transmission destination user.

<3-2. Appropriate Time Slot Determination Process of Apology or Encouragement Message>

Figure 8:
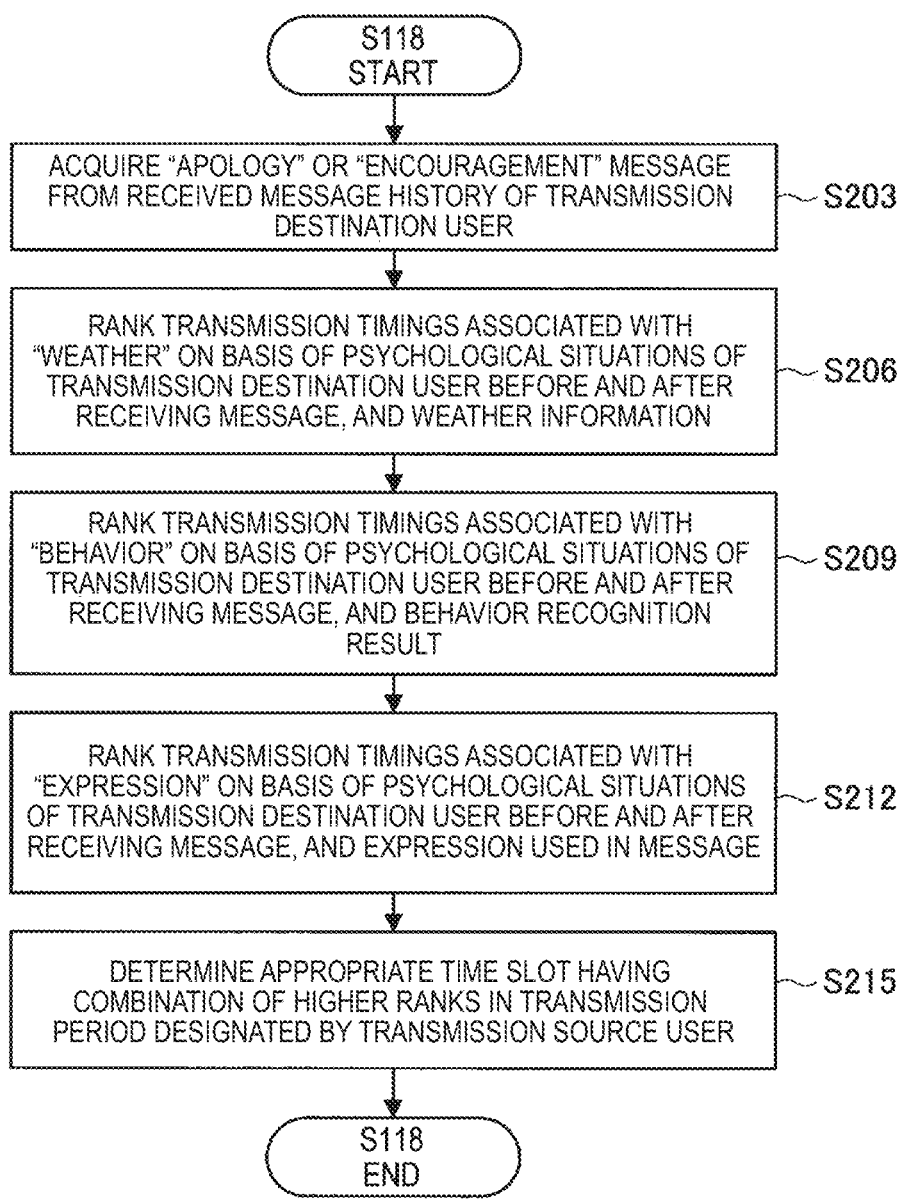
FIG. 8 is a flowchart illustrating an appropriate time slot determination process of an apology or encouragement message according to the embodiment.

Next, details of the determination process in S118 will be described with reference to FIG. 8. FIG. 8 is a flowchart illustrating an appropriate time slot determination process of an apology or encouragement message according to the embodiment.

As illustrated in FIG. 8, the transmission timing determination unit 203 first extracts a message of the same type as the message whose scheduling request has been issued (here, "apology" or "encouragement" message), from a received message history of the transmission destination user stored in the message storage unit 250 (Step S203). In this case, it is also possible for the transmission timing determination unit 203 to extract the message from a message history received from the transmission source user.

Next, the transmission timing determination unit 203 ranks transmission timings associated with "weather" on the basis of psychological situations of the transmission destination user before and after receiving the extracted message, and weather information around the transmission destination user at the time of receiving the message (Step S206). For example, the psychological situations of the transmission destination user are estimated from stability based on the heartbeat information or a questionnaire result. The weather information around the user of the transmission destination is acquired from a position history of the transmission destination user and a weather information history.

Next, the transmission timing determination unit 203 ranks transmission timings associated with "behavior" on the basis of psychological situations of the transmission destination user before and after receiving the extracted message, and a behavior recognition result of the transmission destination user at the time of receiving the message (Step S209).

Next, the transmission timing determination unit 203 ranks transmission timings associated with "expression" on the basis of psychological situations of the transmission destination user before and after receiving the extracted message, and expression used in the message (Step S212).

Next, the transmission timing determination unit 203 determines an appropriate time slot in the transmission period designated by the transmission source user (Step S215). The appropriate time slot has a combination of the "weather", "behavior", and "expression" with higher ranks.

<3-3. Appropriate Time Slot Determination Process of Invitation Message>

Figure 9:
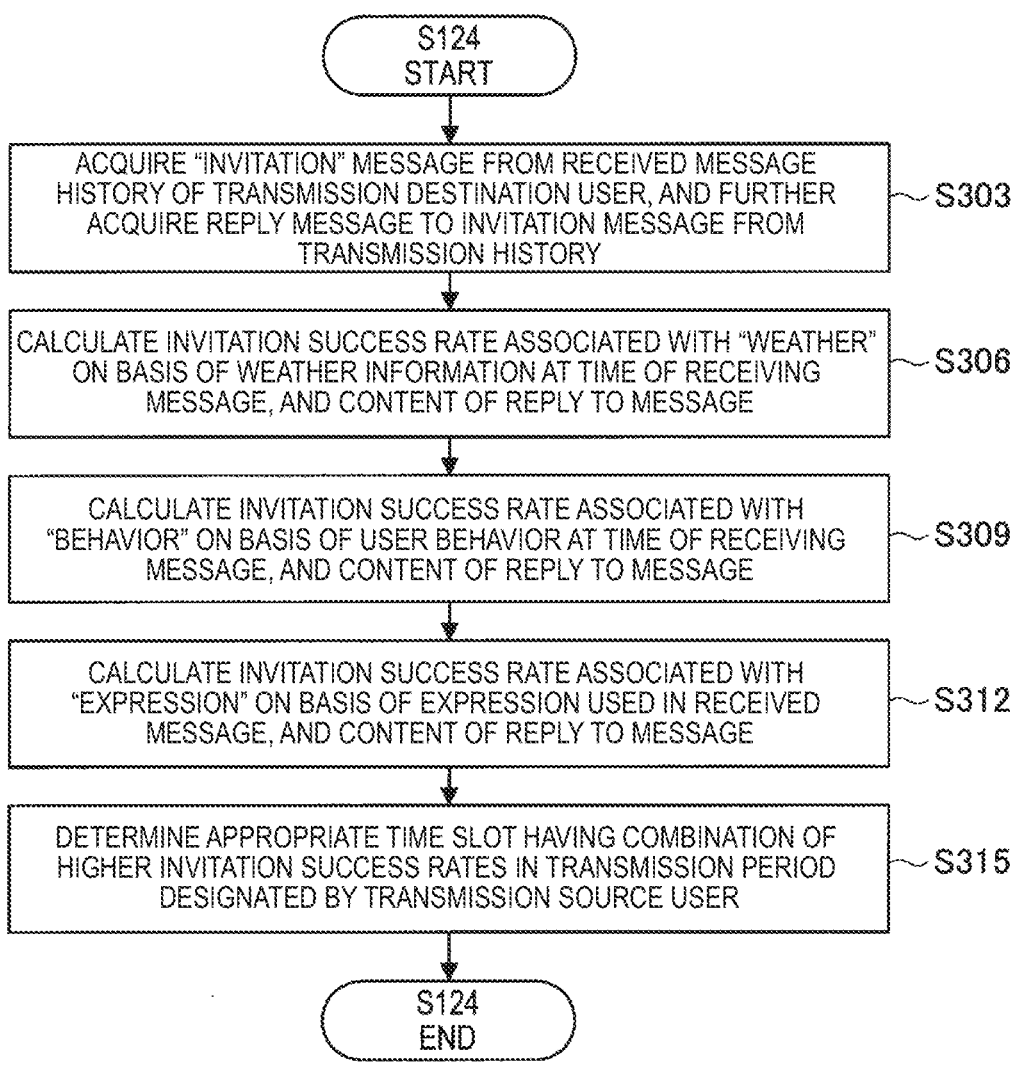
FIG. 9 is a flowchart illustrating an appropriate time slot determination process of an invitation message according to the embodiment.

Next, details of the determination process in S124 will be described with reference to FIG. 9. FIG. 9 is a flowchart illustrating an appropriate time slot determination process of an invitation message according to the embodiment.

As illustrated in FIG. 9, the transmission timing determination unit 203 first extracts a message of the same type as the message whose scheduling request has been issued (here, "invitation" message), from a received message history of the transmission destination user, and further extracts a reply message from the transmission destination user to the extracted invitation message (Step S303). In this case, it is also possible for the transmission timing determination unit 203 to extract the message from a message history received from the transmission source user.

Next, the transmission timing determination unit 203 calculates an invitation success rate associated with "weather" on the basis of weather information around the transmission destination user at the time of receiving the extracted invitation message, and content of the reply message (Step S306). The weather information around the transmission destination user is acquired from a position history of the transmission destination user and a weather information history.

Next, the transmission timing determination unit 203 calculates an invitation success rate associated with "behavior" on the basis of a behavior recognition result of the transmission destination user at the time of receiving the extracted invitation message, and the content of the reply message (Step S309).

Next, the transmission timing determination unit 203 calculates an invitation success rate associated with "expression" on the basis of expression used in the extracted invitation message, and the content of the reply message (Step S312).

Next, the transmission timing determination unit 203 determines an appropriate time slot in the transmission period designated by the transmission source user (Step S315). The appropriate time slot has a combination of the "weather", "behavior", and "expression" with higher invitation success rates.

4. Examples

Next, detailed examples of the information processing system according to the embodiment will be described.

<4-1. Example of Apology Message>

For example, a situation is assumed in which the user A has secretly eaten ice cream in a refrigerator in her house, and the user B who is an older sister of the user A is furious about that because she has wanted to eat that, so the user A wants to apologize for that when the user B gets in a good mood because the user B is in the bad mood now.

The user A creates an apology message to the user B by using the user terminal 1a. In this case, for example, the screen 400 illustrated in the upper side of FIG. 7 is displayed on the user terminal 1a. Next, when the scheduling button 404 is tapped, the screen 410 illustrated in the bottom side of the FIG. 7 is displayed. The user A inputs a transmission period of the input message into the start date and time designation field 411 and the expiration date and time designation field 412, and select modifications to be set by using the modification selection boxes 413. Next, when the scheduling button 415 is tapped, a transmission scheduling request of the input message is transmitted from the user terminal 1a to the server 2.

The transmission scheduling request transmitted to the server 2 is analyzed by the language analysis unit 202, and an overview of the message is interpreted. For example, the language analysis unit 202 determines that the message is an apology message in the case where a keyword such as "sorry", "apologize", or "apology" is extracted from the message whose scheduling request has been issued. On the other hand, in the case where a keyword such as "you can do it" or "believe in you" is extracted, the language analysis unit 202 determines that the message is an encouragement message. In the case of the message "I ate your ice cream in the fridge. Sorry." input in the screen 400 in FIG. 7, the message is determined as an apology message.

Next, the transmission timing determination unit 203 checks the transmission period designated by the user A, acquires a schedule of the user B of the transmission destination in the transmission period from the schedule server 4a, and, on the basis of a time and a place described in the acquired schedule, acquires weather forecast information of that place at that time from the weather information server 4b.

Next, the transmission timing determination unit 203 acquires a position history of the user B, past weather information, and relations between heartbeats (in other words, psychological situations) of the user B and weather situations based on a heartbeat history of the user B, or relations between behavior and heartbeats of the user B based on the heartbeat history and a behavior recognition history of the user B, and estimates a heartbeat value of the user B on the basis of the schedule of the user B, behavior prediction, or weather forecast. Here, FIG. 10 illustrates an example of a heartbeat estimation result corresponding to the schedule of the user B, behavior prediction, and the weather forecast. In the illustrated example, heartbeat values of the user B are estimated on the basis of the schedule of the user B, behavior prediction, and weather forecast during the transmission period (see FIG. 7) from 14:00 to 14:00 on the next day designated by the user A of the transmission source.

Subsequently, the transmission timing determination unit 203 refers to the estimation result and determines a time slot in which the user B has a more stable psychological situation as an appropriate time slot for transmitting the apology message. For example, the stable psychological situation means a state in which heartbeats do not up or down significantly and the heartbeats remain in a relatively slow state. For example, in the case where the heartbeats are estimated to be a predetermined value or lower for a predetermined period of time, the transmission timing determination unit 203 determines that this is a stable time slot. In addition, it is also possible for the transmission timing determination unit 203 to exclude a sleeping time slot from appropriate time slots in view of heartbeats and a sleeping time slot pattern derived from the behavior history. In addition, it is also possible for the transmission timing determination unit 203 to avoid time expected to be time in which the user B is with the user of the transmission source, on the basis of behavior prediction and content of the schedule of the user B.

According to the above-described analysis, for example, the transmission timing determination unit 203 determines that the appropriate time slot for transmitting the apology message is from 15:00 to 16:00 before extracurricular activity, in the case of the example illustrated in FIG. 10.

Note that, in this embodiment, the heartbeats are used for determining the stability of psychological situations. However, the embodiment is not limited thereto. For example, barometric pressure, a discomfort index, or the like may be used. In addition, it is also possible for the transmission timing determination unit 203 to determine a time slot in which a stable psychological situation tends to be obtained as the appropriate time slot for transmitting an apology message, on the basis of a past heartbeat history of the user B. For example, the transmission timing determination unit 203 calculates an average value of heartbeat values acquired for a predetermined period of time, and dispersion of the values, and determines a period of time having a low average value and small dispersion as the stable state.

Next, when the appropriate time slot determined by the transmission timing determination unit 203 comes, the transmission control unit 204 of the server 2 acquires real-time heartbeat information and real-time behavior recognition result of the user B. In the case where heartbeat information and behavior information of the user B are not always acquired, the server 2 remotely causes the user terminal 1*b* and the wearable terminal 10 of the user B to activate the various kinds of sensors for acquiring the heartbeat information and the behavior information.

Next, when it is recognized that heartbeats of the user B is stable and calm and that the user B is sitting for a while from the real-time behavior recognition result and the real-time heartbeat information, the transmission control unit 204 determines that now is the appropriate timing, and transmits the apology message whose scheduling request has been issued by the user A to the user terminal 1*b* of the user B. Note that, in the case where real-time positional information of the user A of the transmission source is also acquired in addition to real-time positional information of the user B of the transmission destination at this time, the transmission control unit 204 does not transmit the message if the user B of the transmission destination is with the person who has transmitted the message (user A).

In addition, in the case where the appropriate timing does not come even at the end of the appropriate time slot, it is possible for the transmission control unit 204 to perform control such that the message is forcibly transmitted due to expiration of the time limit. In this case, it is possible to transmit the message within the determined appropriate time slot though not the appropriate timing.

In addition, in the case where the modification of the message is set, the transmission control unit 204 transmits the apology message that has been automatically edited by the message editing unit 205, to the user B. For example, the message editing unit 205 adds a sentence talking about weather as an opening sentence of the message on the basis of weather and season information at the time of transmission, such as "We got lucky with great weather! By, the way, I ate your ice cream in the fridge. Sorry!".

In addition, the message editing unit 205 changes the wording "Sorry." into the wording "Sorry!" on the basis of the past heartbeat history of the user B receiving apology messages, in the case where the user B has more stable heartbeats when receiving a message with the wording "Sorry!" rather than receiving a message with the wording "Sorry.".

The message transmitted to the user B is stored in the message storage unit 250 of the server 2. It addition, it is possible to use a questionnaire to provide feedback about whether the transmission destination user understands an intention of the message transmitted to the user B. For example, the server 2 transmits a questionnaire to the user B serving as the transmission destination user a few days after the transmission of the message. More specifically, the server 2 displays a questionnaire screen 420 as illustrated in FIG. 11 on the user terminal 1*b* and prompts the user B to answer the questionnaire. In the illustrated example, the questionnaire screen 420 displays questions for asking how the user B feels about the message such as "did you feel a sense of security?", "did you feel honesty?", and "did you feel a sense of affinity?". Answers are input on a five-point scale as illustrated in FIG. 11. The server 2 stores a result of the answers to the questionnaire in the questionnaire result storage unit 260 in association with the user ID and the message reception date and time. In addition, as another way to provide feedback, it is possible to acquire change in heartbeats of the transmission destination user before and after receiving the message. Information of the questionnaire result and the change in heartbeats before and after the reception of a message may be used for automatically editing a transmission timing and a message to be transmitted to the user next time.

<4-2. Example of Encouragement Message>

Next, details of the example of the encouragement message will be described. For example, a case is assumed in which a dance recital of a user C who is a friend of the user A will be held next week, but the user A cannot go or see the recital because the user A lives in a place far apart from the venue, so the user A wants to cheer the user C at a timing that does not bother the user C.

In a way similar to the case of the apology message, the user A inputs an encouragement message such as "Your recital will be on 24th! You can do it!" into the user terminal 1*a*, and taps the scheduling button 404. Next, the user inputs a transmission period, configures setting about modification of the message, and taps the scheduling button 415.

Next, when a message scheduling request is transmitted from the user terminal 1*a*, the server 2 interprets an overview of the message by using the language analysis unit 202. Here, the keyword "You can do it" is extracted. Therefore, the message is determined as an encouragement message.

Next, in a way similar to the above-described example, the transmission timing determination unit 203 estimates heartbeat values (psychological states) of the user C on the basis of a schedule of the transmission destination user C, behavior prediction, or weather forecast during the designated transmission period. Here, FIG. 12 illustrates an example of a heartbeat estimation result corresponding to the schedule of the user C, the behavior prediction, and the weather forecast. In the illustrated example, heartbeat values of the user C are estimated on the basis of the schedule of the user C, the behavior prediction, and the weather forecast during the transmission period from 18th to 23rd designated by the user A of the transmission source.

Subsequently, the transmission timing determination unit 203 refers to the estimation result and determines a time slot in which the encouragement message is more effective to the user C in a psychological state, as an appropriate time slot for transmitting the encouragement message. It may be determined that the which psychological state makes the encouragement message more effective, on the basis of a questionnaire result or change in heartbeats of the user C before and after receiving past encouragement messages to the user C. This is because some people get stable and satisfied in the case of receiving an encouragement message when they are in a stable psychological situation, but some people get stable and satisfied in the case of receiving an encouragement message when they are in an unstable psychological situation. In addition, in a way similar to the above-described example, it is possible to exclude a sleeping time slot from the appropriate time slot, and it is possible to avoid a time slot in which the receiver is with the sender.

For example, the server 2 determines an appropriate time slot for transmitting a message on the basis of weather information, change in heartbeats at the time of reception corresponding to a past encouragement message reception history of the user C, or the like. Specifically, for example, from the past experience, the server 2 recognizes that the encouragement to the user C on the day before the event makes the user U nervous rather than reassuring (stable heartbeats changes into unstable heartbeats), an questionnaire result indicating that the user C gains a feeling of security when the user C gets encouragement while the user C has unstable heartbeats, and that heartbeats of the user C get stable in the case of receiving an encouragement message during raining. In this case, the server 2 refers to a correspondence table of schedule, weather information, behavior, and estimated heartbeats as shown in FIG. 12, and determines that the optimal time slot for transmitting the message is a day other than 23rd that is the day before the recital, a rainy day, and a time slot in which the user C has fast heartbeats and is in an unstable state. That is, the server 2 determines that the optimal time slot is 22th that is two days before the recital.

Next, when 22th comes, the server 2 collects real-time heartbeats and a real-time behavior recognition result of the user C. When it is recognized that the user C has unstable heartbeats and does not stay calm and the user C is sitting for a while, the server 2 determines that now is the appropriate timing, and transmits the encouragement message whose scheduling request has been issued by the user A to a user terminal of the user C.

In addition, in the case where the modification of the message is set, the transmission control unit 204 transmits the encouragement message that has been automatically edited by the message editing unit 205, to the user C. For example, with regard to the message "Your recital will be on 24th! You can do it!", the message editing unit 205 converts the message such that the wording "24th" is interpreted into wording "the day after tomorrow" because the message will be transmitted on 22nd. In addition, the message editing unit 205 converts the message into a message with wording "I believe in you" on the basis of a questionnaire result indicating that the user C has felt a stronger sense of affinity when receiving a message using wording "I believe in you" rather than receiving an encouragement message using wording "you can do it" in the past.

The details of the information processing system configured to transmit a message at an optimal timing have been described above. Accordingly, for example, it is possible to transmit an invitation e-mail, an apology e-mail, and the like to a lover at a most effective timing. Therefore, it is possible to establish a good relationship with the lover.

5. Conclusion

As described above, by using an information processing system according to the embodiment of the present disclosure, it is possible to receive a transmission schedule of a message to a specific receiver and perform control such that the receiver is notified of the message at an optimal timing in view of content of the message and a psychological situation of the receiver.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it is also possible to create a computer program for causing a hardware such as CPU, ROM, and RAM, which are embedded in the above described user terminals 1 or the server 2, to execute the functions of the user terminals 1 or the server 2. Moreover, it may be possible to provide a computer-readable recording medium having the computer program stored therein.

In addition, in the above-described embodiment, an optimal time slot for transmitting a message is determined by using the behavior recognition history, the heartbeat history, and the schedule of the user, weather forecast information, or the like. However, it is not necessary to use all the information in the embodiment. Even when using a piece of the information, it is possible to maximally determine situations, determine the optimal time slot, and automatically edit messages.

In addition, the weather information is used as an example of environmental information. However, the embodiment is not limited thereto. It is also possible to use barometric information acquired by a barometric sensor installed in each of the user terminals 1. In addition, the heartbeat information is used as an example of biological information used for estimating psychological situations. However, the embodiment is not limited thereto. It is also possible to detect and use a body temperature, pulse, breathing, sweating, brain waves, or the like.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A communication system including:

a communication unit configured to receive, from a communication source, a scheduling request for scheduling transmission of a message to a specific communication destination; and a control unit configured to perform control such that the communication destination is notified of existence of the message at a predetermined timing in accordance with content of the message and a current or past psychological situation of a user corresponding to the specific communication destination received by the communication unit.

(2)

The communication system according to (1), in which the control unit determines an appropriate time slot for notifying the communication destination of the existence of the message, in accordance with a schedule of the user in a transmission period designated by the communication source, and a relation between a past schedule or a behavior recognition result of the user and a corresponding past psychological situation.

(3)

The communication system according to (1) or (2), in which the control unit determines an appropriate time slot for notifying the communication destination of the existence of the message, in accordance with weather forecast information in a transmission period designated by the communication source, and a relation between past surrounding weather information of the user and a corresponding past psychological situation.

(4)

The communication system according to (3), in which the weather forecast information and the surrounding weather information include weather, temperature, humidity, barometric pressure, or a discomfort index.

(5)

The communication system according to any one of (1) to (4), in which the control unit determines an appropriate time slot for notifying the communication destination of the existence of the message, in accordance with a psychological situation of the user estimated on a basis of a schedule of the user or weather forecast information in a transmission period designated by the communication source, content of the message received from the communication source, and a relation between content of a past message received by the user and a corresponding past psychological situation.

(6)

The communication system according to any one of (2) to (5), in which the past includes reception date and time of a same type of a past message received by the user as the content of the message to be transmitted.

(7)

The communication system according to any one of (2) to (6), in which the control unit performs control such that the communication destination is notified of existence of the message at an appropriate timing corresponding to a current psychological situation of the user corresponding to the specific communication destination in the determined appropriate time slot.

(8)

The communication system according to (7), in which the control unit performs control such that the communication destination is notified of existence of the message at an appropriate timing further corresponding to a current behavior recognition result of the user corresponding to the specific communication destination.

(9)

The communication system according to any one of (1) to (8), in which the control unit performs control such that the communication destination is notified of existence of a message which is requested by the scheduling request of transmission issued by the communication source, at a predetermined timing on a basis of content of a past message received by the user corresponding to the specific communication destination and a psychological situation of the user at a time of receiving the message that has been received.

(10)

The communication system according to any one of (1) to (9), in which the past psychological situation of the user is estimated on a basis of a result of a questionnaire answered by the user.

(11)

The communication system according to any one of (1) to (9), in which the past psychological situation of the user at the time of receiving the message is estimated on a basis of change in heartbeats of the user before and after receiving the message.

(12)

The communication system according to any one of (1) to (11), in which the control unit inserts a text into the message, the text describing an event occurred after receiving the scheduling request.

(13)

The communication system according to anyone of (1) to (11), in which the control unit changes content of a message which is requested by the scheduling request of the transmission, on a basis of content of a past message received by the user and a psychological situation at the time of receiving the message that has been received.

(14)

The communication system according to any one of (1) to (13), in which, when receiving the scheduling request, the control unit performs control such that a control signal is transmitted to a communication device corresponding to the user, the control signal activating a sensor for detecting a psychological situation of the user corresponding to the specific communication destination.

(15)

The communication system according to any one of (1) to (14), in which the control unit performs control such that a notification of existence of the message is issued when the user currently has a good psychological situation.

(16)

A communication control method including, by a processor:

receiving, from a communication source, a scheduling request for scheduling transmission of a message to a specific communication destination; and performing control such that the communication destination is notified of existence of the message at a predetermined timing in accordance with content of the message and a current or past psychological situation of a user corresponding to the received specific communication destination.

REFERENCE SIGNS LIST 1 user terminal
100 control unit
110 communication unit
120 positional information acquisition unit
130 behavior recognition unit
140 heartbeat information processing unit
150 operation input unit
160 storage unit
170 display unit
180 speaker
190 microphone
2 server
200 control unit
201 history accumulation control unit
202 language analysis unit
203 transmission timing determination unit
204 transmission control unit
205 message editing unit
210 communication unit
220 position history storage unit
230 behavior recognition history storage unit
240 heartbeat history storage unit
250 message storage unit
260 questionnaire result storage unit
3 network
4a schedule server
4b weather information server
10 wearable terminal

The invention claimed is:

1. A communication apparatus, comprising:
processing circuitry configured to:
receive, from a source terminal, a scheduling request for scheduling transmission of a current message to a destination terminal associated with a user;
determine, in response to the scheduling request from the source terminal, a time slot for the transmission of the current message according to content of the current message and a past psychological situation of the user, the past psychological situation being measurable according to biological information history of the user, the biological information history including a heartbeat history, a sweat amount history, a pulse history, or a brain wave history; and within the determined time slot, determine a timing for the transmission of the current message according to the content of the current message and a current psychological situation of the user, the current psychological situation being measurable according to biological information of the user, the biological information including a heartbeat, a sweat amount, a pulse, or a brain wave.

2. The communication apparatus according to claim 1, wherein the processing circuitry is configured to determine the time slot according to a schedule of the user in a transmission period designated by the source terminal and a relation between a past schedule or a behavior recognition result of the user and the past psychological situation.

3. The communication apparatus according to claim 2, wherein the past schedule includes reception date and time of a past message received by the user, the past message and the current message being categorized as a same message type.

4. The communication apparatus according to claim 2, wherein the processing circuitry is configured to determine the timing according to a current behavior recognition result of the user.

5. The communication apparatus according to claim 1, wherein the processing circuitry is configured to determine the time slot according to weather forecast information in a transmission period designated by the source terminal, and a relation between past surrounding weather information of the user and the past psychological situation.

6. The communication apparatus according to claim 5, wherein the weather forecast information and the surrounding weather information include weather, temperature, humidity, barometric pressure, or a discomfort index.

7. The communication apparatus according to claim 1, wherein the processing circuitry is configured to determine the time slot according to an estimated psychological situation of the user estimated on a basis of a schedule of the user or weather forecast information in a transmission period designated by the source terminal, the content of the current message, and a relation between content of a past message received by the user and the past psychological situation.

8. The communication apparatus according to claim 1, wherein the processing circuitry is further configured to notify the destination terminal of existence of the current message at the determined timing.

9. The communication apparatus according to claim 1, wherein the past psychological situation of the user is estimated further based on a basis of a result of a questionnaire answered by the user.

10. The communication apparatus according to claim 1, wherein the past psychological situation of the user is estimated on a basis of change in heartbeats of the user before and after receiving a past message.

11. The communication apparatus according to claim 1, wherein the processing circuitry is configured to insert a text into the current message, the text describing an event occurred after receiving the scheduling request.

12. The communication apparatus according to claim 1, wherein the processing circuitry is configured to change the content of the current message on a basis of content of a past message received by the user and the past psychological situation at a time the past message is received.

13. The communication apparatus according to claim 1, wherein, in response to the receiving the scheduling request, the processing circuitry is configured to transmit a control signal to a communication device associated with the user, the control signal activating a sensor for detecting a psychological situation of the user.

14. The communication apparatus according to claim 1, wherein the processing circuitry is configured to determine a current time within the determined time slot as the timing for the transmission of the current message when the current psychological situation of the user at the current time matches a predetermined psychological situation that is determined according to the content of the current message.

15. A communication method, comprising:
receiving, from a source terminal, a scheduling request for scheduling transmission of a current message to a destination terminal associated with a user;
determining, by processing circuitry of a communication apparatus in response to the scheduling request from the source terminal, a time slot for the transmission of the current message according to content of the current message and a past psychological situation of the user, the past psychological situation being measurable according to biological information history of the user, the biological information history including a heartbeat history, a sweat amount history, a pulse history, or a brain wave history; and
within the determined time slot, determining, by the processing circuitry of the communication apparatus, a timing for the transmission of the current message according to the content of the current message and a current psychological situation of the user, the current psychological situation being measurable according to biological information of the user, the biological information including a heartbeat, a sweat amount, a pulse, or a brain wave.

16. The communication method according to claim 15, wherein the determining the time slot is performed according to a schedule of the user in a transmission period designated by the source terminal and a relation between a past schedule or a behavior recognition result of the user and the past psychological situation.

17. The communication method according to claim 15, wherein the determining the time slot is performed according to weather forecast information in a transmission period designated by the source terminal, and a relation between past surrounding weather information of the user and the past psychological situation.

18. The communication method according to claim 15, wherein the determining the time slot is performed according to an estimated psychological situation of the user estimated on a basis of a schedule of the user or weather forecast information in a transmission period designated by the source terminal, the content of the current message, and a relation between content of a past message received by the user and the past psychological situation.

19. The communication method according to claim 15, further comprising:
notifying the destination terminal of existence of the current message at the determined timing.

20. A communication method, comprising:
receiving, from a source terminal, a scheduling request for scheduling transmission of a message to a destination terminal associated with a user;
determining, by processing circuitry of a communication apparatus in response to the scheduling request from the source terminal, a time slot for the transmission of the message according to content of the message and historical biological information of the user, the historical biological information including first biological measurements provided by the destination terminal prior to the determined time slot; and within the determined time slot, determining, by the processing circuitry of the communication apparatus, a timing for the transmission of the message according to the content of the message and updated biological information of the user, the updated biological information including second biological measurements provided by the destination terminal during the determined time slot.

* * * * *